(12) United States Patent
Kwok

(10) Patent No.: US 6,561,190 B1
(45) Date of Patent: *May 13, 2003

(54) MASK AND A VENT ASSEMBLY THEREFOR

(75) Inventor: Philip R. Kwok, West Pymble (AU)

(73) Assignee: ResMed Limited, North Ryde (AU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/021,541

(22) Filed: Feb. 10, 1998

(30) Foreign Application Priority Data

Feb. 10, 1997 (AU) ................................. PO5045

(51) Int. Cl.$^7$ ............................................. A62B 18/10

(52) U.S. Cl. ........................... 128/207.12; 128/207.16; 128/205.24; 128/204.18; 128/206.12; 128/206.21

(58) Field of Search ....................... 128/207.12, 207.13, 128/207.14, 201.25, 206.12, 205.25, 205.27, 205.28, 206.15, 206.21, 206.22, 863, 204.18, 204.23, 205.24, 200.28, 200.29, 205.13–205.17, 204.22, 206.18

(56) References Cited

U.S. PATENT DOCUMENTS

| 781,516 | A | 1/1905 | Guthrie |
| 812,706 | A | 2/1906 | Warbasse |
| 1,081,745 | A | 12/1913 | Johnston et al. |
| 1,192,186 | A | 7/1916 | Greene |
| 1,653,572 | A | 12/1927 | Jackson |

(List continued on next page.)

FOREIGN PATENT DOCUMENTS

| AU | 77110/91 | * 11/1991 |
| AU | 91/77110 B | 11/1991 |
| AU | 94/64816 B | 12/1994 |
| AU | 95/16178 B | 7/1995 |
| AU | A 32914/95 | 2/1996 |

(List continued on next page.)

OTHER PUBLICATIONS

Mask 1 Photographs, Respironics Inc., Reusable Full Mask (small) Part # 452033 Lot #951108.
Mask 2 Photographs, Puritan—Bennett, Adam Curcuit, Shell Part # 231700, Swivel Part # 616329–00, Pillows (medium) Part #616324.
Mask 3, Photographs, DeVilbiss Healthcare Inc., DeVilbiss Seal–Ring and CPAP Mask Kit (medium), Part 73510–669.
Mask 4 Photographs, Respironics Inc., Monarch Mini Mask with Pressure Port. Part # 572004, Monarch Headgear, Part # 572011.
Mask 5 Photographs, Healthdyne Technologies, Nasal CPAP Mask (medium narrow), Part # 702510.
Mask 6 Photographs, Healthdyne Technologies, Soft Series Nasal CPAP Mask, Part # 702020.
Mask 7 Photographs, DeVilbiss Healthcare Inc., Small Mask and Seal Rings, Part # 73510–668.

(List continued on next page.)

*Primary Examiner*—Aaron J. Lewis
*Assistant Examiner*—Teena Mitchell
(74) *Attorney, Agent, or Firm*—Pillsbury Winthrop LLP

(57) ABSTRACT

A mask (10) for use with a system for supplying breathable gas pressurised above atmospheric pressure to a human or animal's airways. The mask (10) includes a mask shell (12) which is, in use, in fluid communication with a gas supply conduit (30), and a gas washout vent assembly (20). At least the region of the mask shell (12) or conduit (30) surrounding or adjacent the vent assembly is formed from a relatively flexible elastomeric material.

76 Claims, 6 Drawing Sheets

U.S. PATENT DOCUMENTS

| | | | | |
|---|---|---|---|---|
| 1,926,027 | A | 9/1933 | Biggs | |
| 2,123,353 | A | 7/1938 | Catt | |
| 2,248,477 | A | 7/1941 | Lombard | |
| 2,254,854 | A | 9/1941 | O'Connell | |
| 2,317,608 | A | 9/1943 | Heidbrink | |
| 2,371,965 | A | 3/1945 | Lehmberg | |
| 2,376,871 | A | 5/1945 | Fink | |
| 2,415,846 | A | 2/1947 | Randall | |
| 2,438,058 | A | 3/1948 | Kincheloe | |
| 2,578,621 | A | 12/1951 | Yant | |
| 2,931,356 | A | 4/1960 | Schwarz | |
| D188,084 | S | 5/1960 | Garelick | |
| 2,939,458 | A | 6/1960 | Lundquist | |
| 3,013,556 | A | 12/1961 | Galleher | |
| 3,182,659 | A * | 5/1965 | Blount | 128/207.12 |
| 3,189,027 | A | 6/1965 | Bartlett | |
| 3,193,624 | A * | 7/1965 | Webb et al. | 128/207.12 |
| 3,238,943 | A | 3/1966 | Holley | |
| 3,315,674 | A | 4/1967 | Bloom et al. | |
| 3,330,273 | A | 7/1967 | Bennett | |
| 3,362,420 | A | 1/1968 | Blackburn et al. | |
| 3,363,833 | A | 1/1968 | Laerdal | |
| 3,556,122 | A | 1/1971 | Laerdal | |
| 3,580,051 | A | 5/1971 | Blevins | |
| 3,680,556 | A * | 8/1972 | Morgan | 128/201.15 |
| 3,700,000 | A | 10/1972 | Hesse et al. | |
| 3,720,235 | A | 3/1973 | Schrock | |
| 3,796,216 | A | 3/1974 | Schwarz | |
| 3,799,164 | A | 3/1974 | Rollins | |
| D231,803 | S | 6/1974 | Huddy | |
| 3,877,425 | A * | 4/1975 | O'Neill | 128/202.19 |
| 3,958,275 | A * | 5/1976 | Morgan et al. | 128/201.27 |
| 4,077,404 | A | 3/1978 | Elam | |
| D250,131 | S | 10/1978 | Lewis et al. | |
| 4,167,185 | A | 9/1979 | Lewis | |
| 4,219,020 | A * | 8/1980 | Czajka | 128/207.13 |
| 4,226,234 | A | 10/1980 | Gunderson | |
| 4,245,632 | A | 1/1981 | Houston | |
| 4,274,406 | A * | 6/1981 | Bartholomew | 128/204.25 |
| D262,322 | S | 12/1981 | Mizerak | |
| 4,304,229 | A | 12/1981 | Curtin | |
| 4,328,797 | A | 5/1982 | Rollins, III et al. | |
| 4,347,205 | A | 8/1982 | Stewart | |
| 4,354,488 | A | 10/1982 | Bartos | |
| 4,402,316 | A | 9/1983 | Gadberry | |
| 4,412,537 | A | 11/1983 | Tiger | |
| 4,454,881 | A * | 6/1984 | Huber et al. | 128/206.15 |
| 4,467,799 | A | 8/1984 | Steinberg | |
| 4,522,639 | A | 6/1985 | Ansite et al. | |
| 4,558,710 | A | 12/1985 | Eichler | |
| 4,616,647 | A | 10/1986 | McCreadie | |
| 4,622,964 | A | 11/1986 | Flynn | |
| 4,655,213 | A | 4/1987 | Rapoport et al. | |
| 4,665,570 | A | 5/1987 | Davis | |
| 4,671,271 | A | 6/1987 | Bishop et al. | |
| 4,677,975 | A | 7/1987 | Edgar et al. | |
| 4,677,977 | A | 7/1987 | Wilcox | |
| D293,613 | S | 1/1988 | Wingler | |
| 4,739,755 | A * | 4/1988 | White et al. | 128/206.12 |
| 4,770,169 | A | 9/1988 | Schmoegner et al. | |
| 4,774,941 | A | 10/1988 | Cook | |
| 4,782,832 | A | 11/1988 | Trimble et al. | |
| 4,799,477 | A * | 1/1989 | Lewis | 128/206.24 |
| 4,809,692 | A | 3/1989 | Nowacki et al. | |
| 4,819,629 | A | 4/1989 | Jonson | |
| 4,821,713 | A | 4/1989 | Bauman | |
| 4,841,953 | A | 6/1989 | Dodrill | |
| 4,848,334 | A | 7/1989 | Bellm | |
| 4,848,366 | A | 7/1989 | Aita et al. | |
| 4,907,584 | A | 3/1990 | McGinnis | |
| 4,910,806 | A | 3/1990 | Baker et al. | |
| 4,919,128 | A | 4/1990 | Kopala et al. | |
| 4,938,210 | A | 7/1990 | Shene | |
| 4,938,212 | A | 7/1990 | Gnook et al. | |
| 4,944,310 | A | 7/1990 | Sullivan | |
| D310,431 | S | 9/1990 | Bellm | |
| 4,971,051 | A | 11/1990 | Toffolon | |
| 4,974,586 | A * | 12/1990 | Wandel et al. | 128/206.28 |
| 4,986,269 | A | 1/1991 | Hakkinen | |
| 4,989,596 | A * | 2/1991 | Moreis et al. | 128/207.12 |
| 4,989,599 | A | 2/1991 | Carter | |
| 5,005,568 | A | 4/1991 | Loescher et al. | |
| 5,005,571 | A | 4/1991 | Dietz | |
| 5,018,519 | A * | 5/1991 | Brown | 128/203.29 |
| 5,038,776 | A | 8/1991 | Harrison et al. | |
| 5,042,473 | A | 8/1991 | Lewis | |
| 5,042,478 | A | 8/1991 | Kopala et al. | |
| 5,046,200 | A | 9/1991 | Feder | |
| 5,063,922 | A | 11/1991 | Hakkinen | |
| 5,065,756 | A * | 11/1991 | Rapoport | 128/204.18 |
| 5,069,205 | A | 12/1991 | Urso | |
| 5,080,094 | A * | 1/1992 | Tayebi | 128/205.29 |
| D323,908 | S | 2/1992 | Hollister et al. | |
| 5,109,839 | A * | 5/1992 | Blasdell et al. | 128/203.12 |
| 5,109,840 | A | 5/1992 | Daleiden | |
| 5,121,745 | A | 6/1992 | Israel | |
| 5,133,347 | A | 7/1992 | Huennebeck | |
| 5,140,980 | A * | 8/1992 | Haughey et al. | 128/201.25 |
| 5,140,982 | A | 8/1992 | Bauman | |
| 5,159,938 | A | 11/1992 | Laughlin | |
| 5,178,138 | A | 1/1993 | Walstrom et al. | |
| D334,633 | S | 4/1993 | Rudolph | |
| 5,231,983 | A | 8/1993 | Matson et al. | |
| 5,233,978 | A | 8/1993 | Callaway | |
| 5,243,971 | A * | 9/1993 | Sullivan et al. | 128/204.18 |
| 5,265,595 | A | 11/1993 | Rudolph | |
| 5,279,289 | A | 1/1994 | Kirk | |
| 5,280,784 | A | 1/1994 | Kohler | |
| 5,297,544 | A * | 3/1994 | May et al. | 128/202.22 |
| 5,311,862 | A | 5/1994 | Blasdell et al. | |
| 5,322,057 | A | 6/1994 | Raabe et al. | |
| 5,343,878 | A | 9/1994 | Scarberry et al. | |
| 5,357,951 | A | 10/1994 | Ratner | |
| 5,368,020 | A * | 11/1994 | Beux | 128/204.22 |
| 5,372,130 | A | 12/1994 | Stern et al. | |
| 5,388,571 | A | 2/1995 | Roberts et al. | |
| 5,404,871 | A | 4/1995 | Goodman et al. | |
| 5,419,318 | A | 5/1995 | Tayebi | |
| 5,429,126 | A | 7/1995 | Bracken | |
| 5,429,683 | A | 7/1995 | Le Mitouard | |
| 5,431,158 | A | 7/1995 | Tirotta | |
| 5,438,981 | A | 8/1995 | Starr et al. | |
| 5,441,046 | A | 8/1995 | Starr et al. | |
| D362,061 | S | 9/1995 | McGinnis et al. | |
| 5,477,852 | A * | 12/1995 | Landis et al. | 128/207.18 |
| 5,479,920 | A | 1/1996 | Piper et al. | |
| 5,488,948 | A | 2/1996 | Dubruille et al. | |
| 5,492,116 | A | 2/1996 | Scarberry et al. | |
| 5,501,214 | A | 3/1996 | Sabo | |
| 5,509,404 | A | 4/1996 | Lloyd et al. | |
| 5,517,986 | A | 5/1996 | Starr et al. | |
| 5,538,000 | A | 7/1996 | Rudolph | |
| 5,540,223 | A | 7/1996 | Starr et al. | |
| 5,542,128 | A | 8/1996 | Lomas | |
| 5,546,936 | A * | 8/1996 | Visag et al. | 128/207.14 |
| RE35,339 | E * | 10/1996 | Rapoport | 128/204.18 |
| 5,560,354 | A | 10/1996 | Berthon-Jones et al. | |
| 5,570,682 | A | 11/1996 | Johnson | |
| 5,570,689 | A | 11/1996 | Starr et al. | |
| D377,089 | S | 12/1996 | Starr et al. | |
| 5,592,938 | A | 1/1997 | Scarberry et al. | |

| | | | | | | |
|---|---|---|---|---|---|---|
| 5,608,647 A | 3/1997 | Rubsamen et al. | | EP | 0 821 978 | 2/1998 |
| 5,642,730 A | 7/1997 | Baran | | FR | 2 574 657 A1 | 6/1986 |
| 5,645,049 A | * 7/1997 | Foley et al. | 128/203.29 | FR | 2 658 725 A1 | 8/1991 |
| 5,647,355 A | 7/1997 | Starr et al. | | FR | 2 749 176 | 12/1997 |
| 5,647,357 A | 7/1997 | Barnett et al. | | GB | 1395391 | 5/1975 |
| 5,649,532 A | 7/1997 | Oren | | GB | 1 467 828 | 3/1977 |
| 5,649,533 A | 7/1997 | Griffiths | | GB | 2145335 A | 3/1985 |
| 5,655,520 A | 8/1997 | Howe et al. | | GB | 2147506 A | 5/1985 |
| 5,655,527 A | 8/1997 | Scarberry et al. | | GB | 2 164 569 A | 3/1986 |
| 5,657,493 A | 8/1997 | Ferrero et al. | | GB | 2 267 648 A | 12/1993 |
| 5,657,752 A | * 8/1997 | Landis et al. | 128/207.13 | JP | 09/216240 A | 8/1997 |
| 5,662,101 A | 9/1997 | Ogden et al. | | WO | WO 80/01044 | 5/1980 |
| 5,666,946 A | 9/1997 | Langenback | | WO | WO 82/03548 | 10/1982 |
| 5,685,296 A | 11/1997 | Zdrojkowski et al. | | WO | WO 86/06969 | 12/1986 |
| 5,687,715 A | 11/1997 | Landis et al. | | WO | WO 87/01950 | 4/1987 |
| 5,715,814 A | 2/1998 | Ebers | | WO | WO 91/03277 | 3/1991 |
| 5,732,695 A | * 3/1998 | Metzger | 128/206.12 | WO | WO 92/15353 | 9/1992 |
| 5,746,201 A | 5/1998 | Kidd | | WO | WO 92/20395 | 11/1992 |
| 5,813,423 A | 9/1998 | Kirchgeorg | | WO | WO 93/01854 | 2/1993 |
| 5,832,918 A | 11/1998 | Pantino | | WO | WO 94/02190 | 2/1994 |
| 6,006,748 A | * 12/1999 | Hollis | 128/205.24 | WO | WO 94/16759 | 8/1994 |
| 6,019,101 A | * 1/2000 | Cotner et al. | 128/207.13 | WO | WO 94/20051 | 9/1994 |
| 6,135,109 A | * 10/2000 | Blasdell et al. | 128/206.28 | WO | WO 95/02428 | 1/1995 |
| | | | | WO | WO 96/17643 | 6/1996 |
| | | | | WO | WO 96/25983 | 8/1996 |

FOREIGN PATENT DOCUMENTS

| | | |
|---|---|---|
| AU | 9459430 | 2/1996 |
| AU | A 41018/97 | 4/1998 |
| AU | A 89312/98 | 1/1999 |
| CA | 1039144 | 9/1978 |
| DE | 459104 | 4/1928 |
| DE | 701 690 | 1/1941 |
| DE | 159396 | 6/1981 |
| DE | 3015279 A1 | 10/1981 |
| DE | 3345067 A1 | 6/1984 |
| DE | 3537507 A1 | 4/1987 |
| DE | 3539073 A1 | 5/1987 |
| DE | 4004157 C1 | 4/1991 |
| DE | WO 94/01290 * | 2/1994 |
| DE | 4343205 A1 | 6/1995 |
| DE | 197 35 359 | 1/1998 |
| DE | 297 23 101 | 7/1998 |
| DE | 298 10846 U1 | 8/1998 |
| EP | 0 054 154 | 10/1981 |
| EP | 0 252 052 A1 | 1/1988 |
| EP | 0 264 772 A1 | 4/1988 |
| EP | 0 386 605 A1 | 2/1990 |
| EP | 0427474 A2 | 5/1991 |
| EP | 0 462 701 A1 | 12/1991 |
| EP | 0 602 424 | 11/1993 |
| EP | 0 608 684 A1 | 8/1994 |
| EP | 0697 225 A2 | 7/1995 |
| EP | 0 697 225 | 7/1995 |
| EP | 178 925 A2 | 4/1996 |
| EP | 0 747 078 A2 | 12/1996 |
| WO | WO 96/39206 | 12/1996 |
| WO | WO 97/07847 | 3/1997 |
| WO | WO 97/41911 | 11/1997 |
| WO | WO 98/04310 | 2/1998 |
| WO | WO 98/11930 | 3/1998 |
| WO | WO 98/18514 | 5/1998 |
| WO | WO 98/24499 | 6/1998 |
| WO | WO 98/26829 | 6/1998 |
| WO | WO 98/26830 | 6/1998 |
| WO | WO 98/48878 | 11/1998 |

OTHER PUBLICATIONS

Mask 8 Photographs, Respironics Inc., Reusable Contour Mask (medium), Part # 302180.
Mask 9 Photographs, Healthdyne Technologies, Healthdyne Large Headgear.
Mask 10 Photographs, Respironics Inc., Soft Cap (medium), Part # 302142.
Mask 11 Photographs, Weinmann: Hamburg, Nasalmaskensystem mit Schalldämpfer (medium), Part # WN 23105.
Mask 12 Photographs, Life Care.
Mask 13 Photographs, Healthdyne Technologies.
Mask 14 Photograph, King System.
Mask 15 Photographs, Respironics Inc., Paediatric Mask.
Mask 16 Photographs, Hans Rudolph Inc., Hans Rudolph Silicone Rubber Face Mask/8900.

* cited by examiner

MASK AND A VENT ASSEMBLY THEREFOR

FIELD OF THE INVENTION

The present invention relates to a mask and a vent assembly therefor.

The mask and vent assembly according to the invention have been developed primarily for the venting of washout gas in the application of continuous positive airway pressure (CPAP) treatment in conjunction with a system for supplying breathable gas pressurised above atmospheric pressure to a human or animal. Such a system is used, for example, in the treatment of obstructive sleep apnea (OSA) and similar sleep disordered breathing conditions. However, the invention is also suitable for other purposes including, for example, the application of assisted ventilation or respiration.

The term "mask" is herein intended to include face masks, nose masks, mouth masks, nasal pillows, appendages in the vicinity of any of these devices and the like.

BACKGROUND OF THE INVENTION

Treatment of OSA by CPAP flow generator systems involves the continuous delivery of air (or other breathable gas) pressurised above atmospheric pressure to a patient's airways via a conduit and a mask.

For either the treatment of OSA or the application of assisted ventilation, the pressure of the gas delivered to a patient can be at a constant level, bi-level (ie. in synchronism with patient inspiration and expiration) or autosetting in level to match therapeutic need. Throughout this specification the reference to CPAP is intended to incorporate a reference to any one of, or combinations of, these forms of pressure delivery.

The masks used in CPAP treatment generally include a vent for washout of the gas to atmosphere. The vent is normally located in the mask or in the gas delivery conduit adjacent the mask. The washout of gas through the vent is essential for removal of exhaled gases from the breathing circuit to prevent carbon dioxide "re-breathing" or build-up, both of which represent a health risk to the mask wearer. Adequate gas washout is achieved by selecting a vent size and configuration that will allow a minimum safe gas flow at the lowest operating CPAP pressure, which, typically can be as low as around 4 cm $H_2O$ for adults and 2 cm $H_2O$ in paediatric applications.

Prior art masks are generally comprised of a rigid plastic shell which covers the wearer's nose and/or mouth. A flexible or resilient rim (or cushion) is attached to the periphery of the shell which abuts and seals against the wearer's face to provide a gas-tight seal around the nose and/or mouth.

A prior art washout vent utilized one or more holes or slits in the rigid shell or in a rigid portion of the delivery conduit to allow the washout gas to vent to atmosphere. In some masks, the holes or slits were formed during the moulding process. In others, they were drilled or cut as a separate step after the shell or conduit had been moulded.

The flow of gas out the holes or slits in the shell or conduit to atmosphere creates noise and turbulence at the hole or slit outlet as the delivered gas, and upon expiration, the patient-expired gas (including $CO_2$) exits. Bi-level and autosetting gas delivery regimes tend to generate more noise than a constant level gas delivery regime. This is thought to be due to the extra turbulence created by the gas accelerating and decelerating as it cycles between relatively low and relatively high pressures. The noise adversely affects patient and bed-partner comfort.

Another prior art vent included hollow rivets or plugs manufactured from stainless steel or other rigid materials attached to openings in the rigid shell. The outer edges of the rivets were rounded to help reduce noise. However, this approach was expensive, required an extra production step and did not prove effective in reducing noise.

Another approach to reduce noise involved the use of sintered filters at the gas outlet of the mask shell. However, the filters were prone to blocking, especially in the presence of moisture. Accordingly, sintered filters were impractical for use in CPAP treatment as they were easily blocked by the moisture from the patient's respiratory system or humidifiers or during the necessary regular cleaning of the mask and associated componentry.

Foam filters wrapped around the air outlets in the shell were also attempted. However, they also suffered from the disadvantages of being prone to blocking, difficult to clean and requiring constant replacement.

Remote outlet tubes have been used to distance the noise source from the patient. However, these tubes are difficult to clean, are prone to entanglement by the patient and/or their bed partner and suffer the further disadvantage that a volume of exhausted gas is retained in the tube adjacent the mask.

It is an object of the present invention to substantially overcome or at least ameliorate the prior art disadvantages and, in particular, to reduce the noise generated by gas washout through a mask.

SUMMARY OF THE INVENTION

Accordingly, the invention, in a first aspect, discloses a mask for use with a system for supplying breathable gas pressurised above atmospheric pressure to a human or animal's airways, the mask includes a mask shell which is, in use, in fluid communication with a gas supply conduit, a gas washout vent assembly, wherein at least the region of the mask shell or conduit surrounding or adjacent the vent assembly is formed from a relatively flexible elastomeric material.

In an embodiment, the entire mask is formed from the elastomeric material.

In another embodiment, the mask shell and/or conduit is formed from a relatively rigid material and the region surrounding or adjacent the vent assembly is formed from the relatively flexible elastomeric material.

In a second aspect, the invention discloses a vent assembly for the washout of gas from a mask or conduit used with a system for supplying breathable gas pressurized above atmospheric pressure to a human or animal, wherein the vent assembly is formed from the relatively flexible elastomeric material.

In a preferred embodiment, the vent assembly is an insert of relatively flexible elastomeric material, wherein the insert is attachable to the mask shell or conduit. The insert preferably has at least one orifice therethrough.

In a preferred form, the rigid plastics mask shell is formed from polycarbonate and the insert is formed from Silastic™ or Santoprene™.

Desirably, the insert is substantially crescent-shaped and includes a plurality of orifices therethrough.

The insert preferably includes a groove around its periphery, the groove adapted to locate the insert against a correspondingly sized rim of an opening formed in the mask shell or conduit.

In other embodiments, the insert is substantially circular, triangular, cross or peanut shaped.

The mask shell and/or the conduit can desirably also include one or more inserts.

BRIEF DESCRIPTION OF THE DRAWINGS

Preferred embodiments of the invention will now be described, by way of examples only, with reference to the accompanying drawings in which.

DESCRIPTION OF THE PREFERRED EMBODIMENTS

Figure 1:
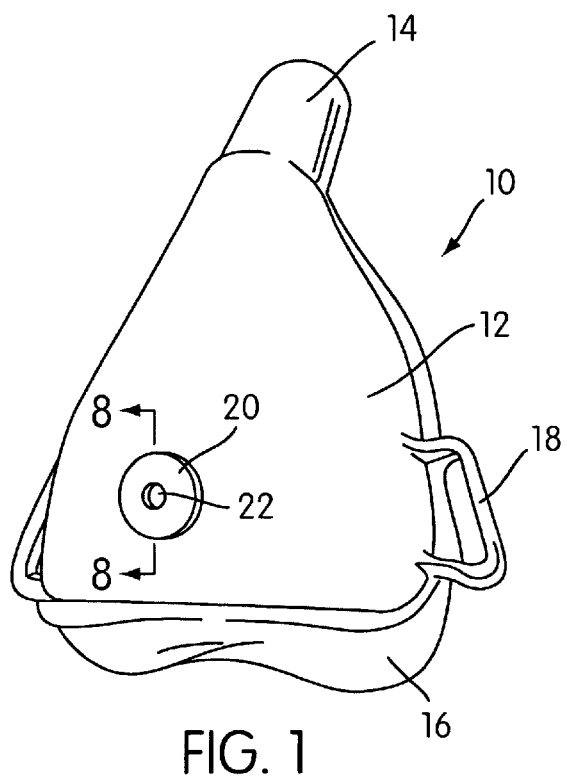
FIG. 1 is a perspective view of a first embodiment.
Figure 2:
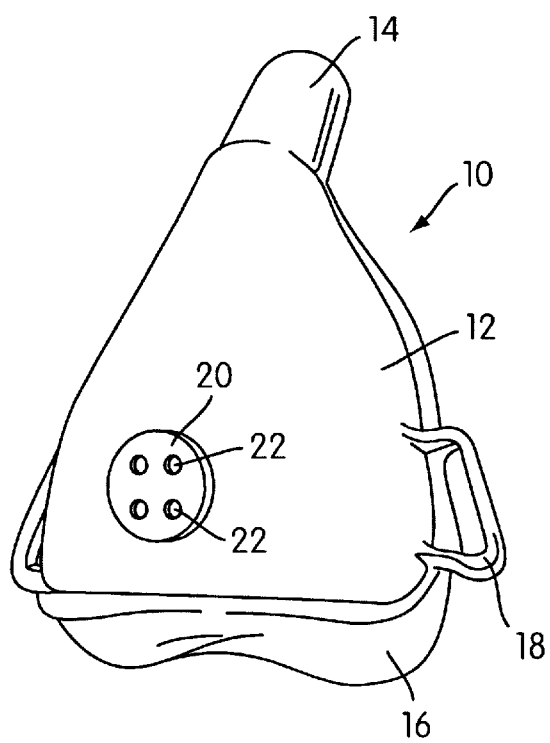
FIG. 2 is a perspective view of a second embodiment.

Referring firstly to FIG. 1, there is shown a mask 10 for use with a system (not shown) for supplying breathable gas pressurised above atmospheric pressure to a human or animal's airways. The mask includes a rigid plastics shell 12 having an inlet tube 14 for connection to a supply conduit to communicate breathable gas from a flow generator (not shown) to the nasal passages of the mask wearer. The mask shell 12 also includes a flexible sealing membrane 16 which is used to provide a gas tight seal between the face of the wearer and the interior of the shell 12. The shell 12 also includes lugs 18 for connecting the mask 10 to a head strap (not shown) to retain the mask in place.

Figure 8:
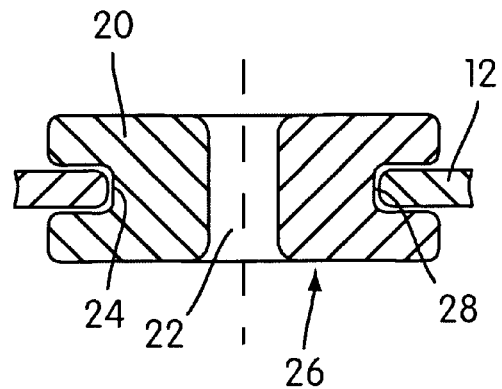
FIG. 8 is a partial cross-sectional view of the first embodiment along the line 8—8 of FIG. 1.

The mask includes a Silastic™ insert 20 through which is provided an orifice 22 for gas washout. As best shown in FIG. 8, the insert 20 has a recess or groove 24 around its periphery. A correspondingly sized opening 26 bounded by a rim 28 is provided in the shell 12 to enable the insert 20 to be retained in place in the fashion of a grommet. The opening 26 can be moulded in the shell 12 or drilled or punched as a post-moulding step. The flexibility of the Silastic™ allows the insert 20 to be initially squeezed through the opening 26 before resiliently expanding to the configuration shown in FIG. 8 and engaging the rim 28.

FIGS. 2 to 7 show further embodiments in which corresponding reference numerals are used to indicate like features. In all these embodiments the insert 20 has an external groove or recess 24 which engages the rim 28 of a correspondingly shaped opening 26 in the mask shell 12 to retain the insert 20 in place.

In the embodiment shown in FIGS. 2 to 5 and 7 the insert 20 includes more than one orifice 22. In the embodiment shown in FIG. 6, two inserts 20 are provided in the shell 12.

Figure 9:
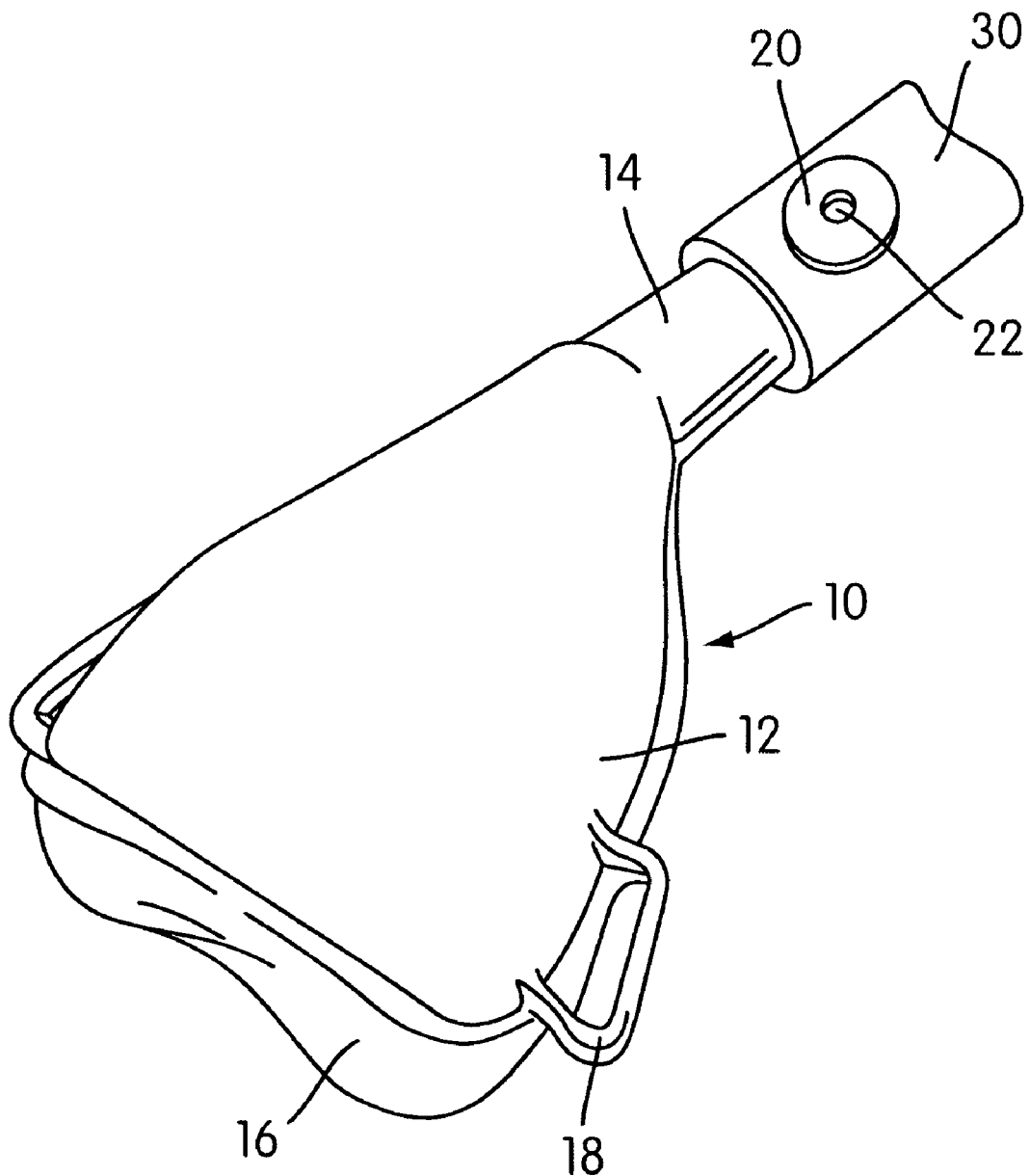
FIG. 9 is a perspective view of an eighth embodiment.

In the embodiment shown in FIG. 9, the insert 20 is provided in a gas supply conduit 30.

Figure 3:
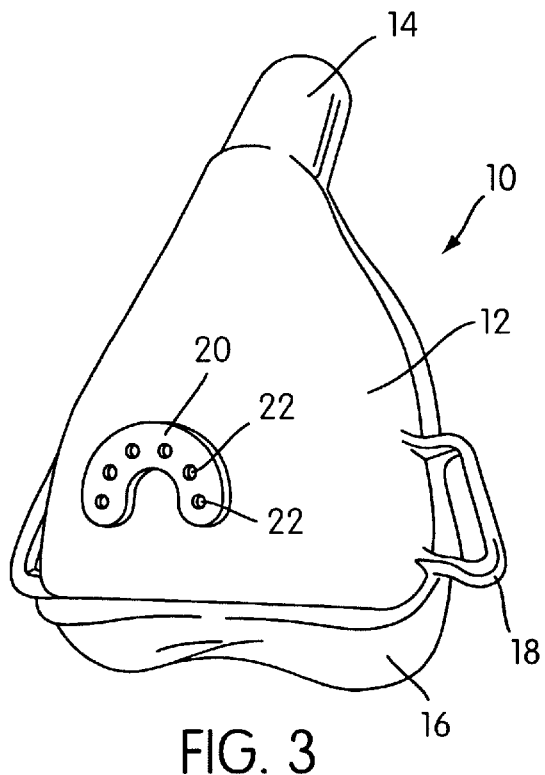
FIG. 3 is a perspective view of a third embodiment.
Figure 4:
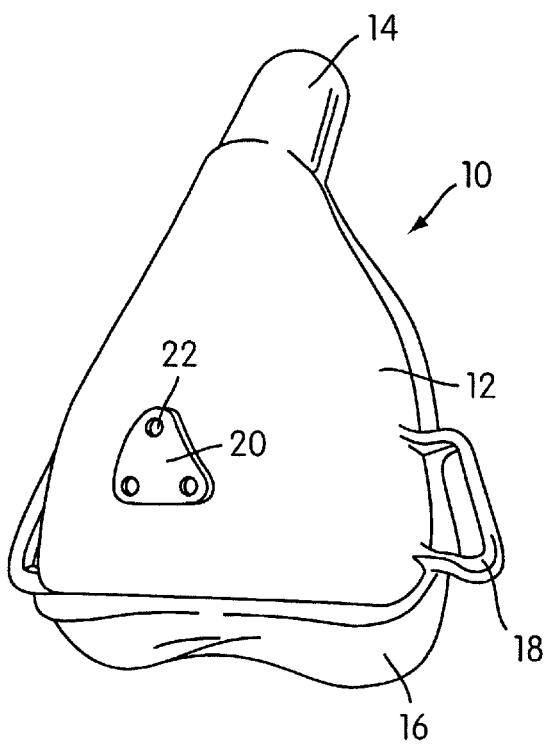
FIG. 4 is a perspective view of a fourth embodiment.
Figure 5:
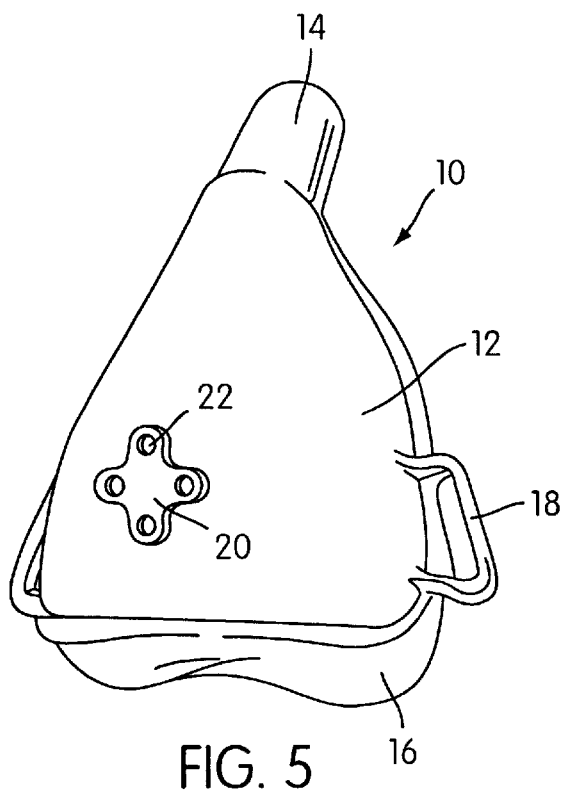
FIG. 5 is a perspective view of a fifth embodiment.
Figure 6:
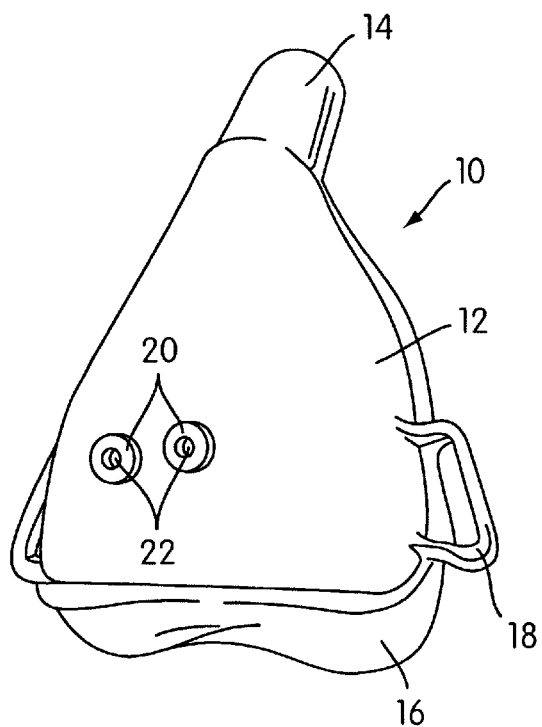
FIG. 6 is a perspective view of a sixth embodiment.
Figure 7:
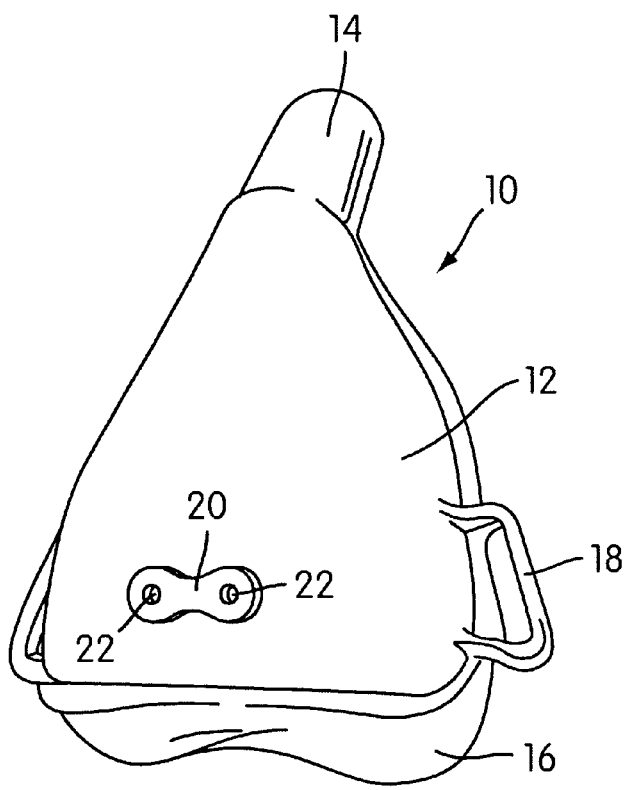
FIG. 7 is a perspective view of a seventh embodiment.
Figure 10:
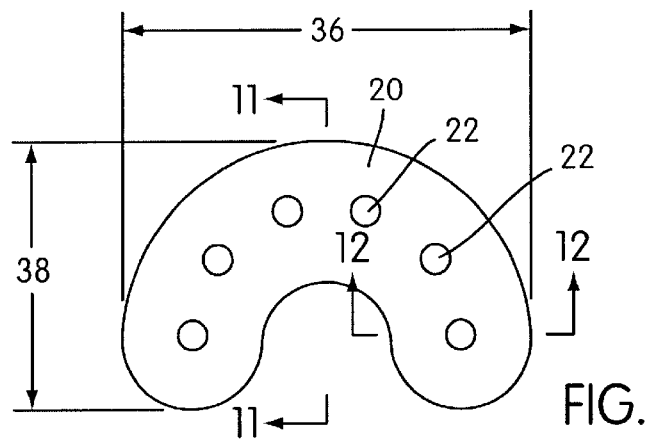
FIG. 10 is a plan view of the insert of the third embodiment.
Figure 11:
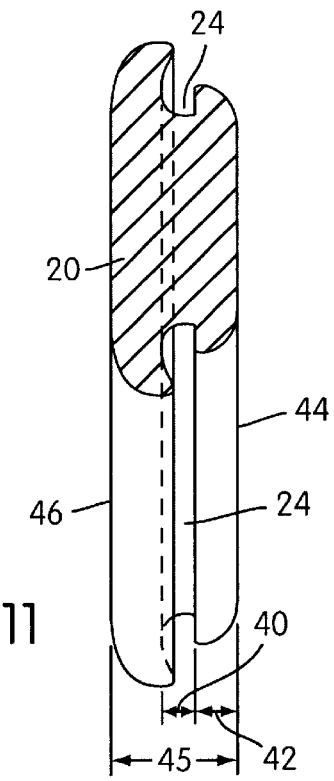
FIG. 11 is a cross-sectional view of the third embodiment insert along the line 11—11 of FIG. 10.
Figure 12:
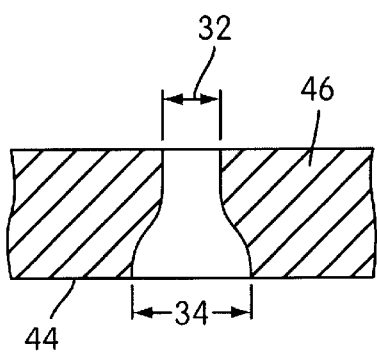
FIG. 12 is a partial cross-sectional view of the third embodiment insert along the line 12—12 of FIG. 10.

FIGS. 10 to 12 show the insert 20 of the third embodiment of FIG. 3. The dimensions 32, 34, 36, 38, 40, 42 and 45 are approximately diameter 1.73 mm, diameter 3.30 mm, 28.80 mm, 19.00 mm, 1.20 mm, 1.20 mm and 3.60 mm respectively.

The side 44 of the insert 20 faces the patient's face in use and the side 46 faces atmosphere.

The mask shell 12 is manufactured from polycarbonate. Other rigid plastics materials can equally be used. The insert 20 can be manufactured from an elastomer sold as Silastic™ (produced by the Dow Corning Corporation) or a thermoplastic elastomer sold as Santoprene™ (produced by Monsanto). Other flexible elastomeric materials can be used also.

The mask 10 produces less noise than an identical mask having a similar sized and shaped orifice(s) formed directly in the mask shell 12 instead of formed in the flexible insert 20. It is thought that the noise reduction occurs due to the flexible insert 20 damping vibrations caused by air passage through the orifice(s) 22 which produce vibrations or similar in the mask shell 12.

A prototype of the embodiment of the invention shown in FIG. 3 has been tested over a range of constant and bi-level CPAP treatment pressures. For comparison purposes, an identical mask to that shown in FIG. 3 but formed entirely from polycarbonate and having six identical arcuately spaced boles 22 drilled directly through the mask shell was also tested. In both masks the six holes had a diameter of 1.7 mm. The results of the test are summarised in the Tables below:

TABLE 1

| Pressure | Constant level gas delivery | |
|---|---|---|
| | Noise levels 1 m from mask (dBA) | |
| (cm H₂O) | With flexible insert | Without flexible insert |
| 4 | 26.8 | 35.2 |
| 10 | 33.4 | 43.1 |
| 18 | 39.3 | 49.2 |

TABLE 2

| Pressure | Bi-level gas delivery | |
|---|---|---|
| | Noise levels 1 m from mask (dBA) | |
| (cm H₂O) | With flexible insert | Without flexible insert |
| 5–10 | 30.8–38.5 | 37.2–43.0 |
| 10–15 | 38.6–43.7 | 42.9–47.9 |

As the results show, the mask shown in FIG. 3 produced less radiated noise than a similar mask not including the flexible elastomeric insert 20 representing a significant advantage in terms of the comfort of the mask wearer and their bed partner.

In addition to the noise reduction discussed above, the masks 10 possesses other advantages over those of the prior art. Firstly, the insert 20 is very easy to install into the mask shell 12 during either assembly of the mask which, is often supplied in kit form, or before and after cleaning which is regularly required and often carried out in the home environment. Secondly, the mask shell 12 may be produced with a single size of opening 26 and provided with a range of different inserts 20 which allows the outlet size to be "tuned" to give an optimum gas washout rate for a particular patient's treatment pressure level.

Although the invention has been described with reference to specific examples, it will be appreciated by those skilled in the art, that the invention may be embodied in many other forms.

I claim:

1. A mask assembly for use with a system for supplying breathable gas pressurized above atmospheric pressure to a human or animal patient's airways, the mask assembly comprising:

(a) a mask which is adapted for fluid connection with a gas supply conduit, (b) a region of the mask defining a first venting orifice adapted for gas washout, and (c) an insert formed of an elastomeric material positioned within said first venting orifice, said insert having at least one orifice therethrough for gas washout, said at least one orifice having a cross-sectional contour from a side of the orifice on the patient's side of the mask to an atmosphere side of the orifice, the cross-sectional contour remaining substantially constant in size as gas is passed therethrough.

2. A mask assembly as in claim 1, wherein the mask is formed from an elastomeric material.

3. A mask assembly as in claim 1, wherein the mask is formed from a material that is relatively rigid compared to the elastomeric material of the insert.

4. A mask assembly as in claim 3 wherein the relatively rigid material is polycarbonate and the elastomeric material is selected from the group consisting of Silastic™ and Santoprene™.

5. A mask assembly as in claim 1, wherein the insert is substantially crescent-shaped and includes a plurality of orifices therethrough.

6. A mask assembly as in claim 1, wherein the insert comprises a groove around a periphery of the insert, the groove being adapted to locate the insert against a correspondingly sized rim of the first venting orifice.

7. A mask assembly as in claim 1, wherein the insert is selected from a shape consisting of substantially circular, triangular, cross or peanut shaped.

8. A mask assembly as in claim 1, wherein the mask includes a plurality of said inserts.

9. A mask assembly in claim 1, wherein a portion of the cross-sectional contour of the orifice near the atmosphere side of the orifice is smaller than a portion of the cross-sectional contour of the orifice near the side of the orifice on the patient's side of the mask.

10. A mask assembly as in claim 1, wherein a central portion of the cross-sectional contour of the orifice has a constant diameter.

11. A mask assembly as in claim 1, wherein the cross-sectional contour of the orifice is symmetrical between the side of the orifice on the patient's side and the atmosphere side of the orifice.

12. A mask assembly as in claim 1, wherein the cross-sectional contour of the orifice is asymmetrical between the side of the orifice on the patient's side of the mask and the atmosphere side of the orifice.

13. A vent assembly for washout of gas from a mask having a vent opening used with a system for supplying breathable gas pressurized above atmospheric pressure to a human or animal patient, comprising:

an insert formed from an elastomeric material, said insert having at least one orifice therethrough for gas washout, said at least one orifice having a cross-sectional contour from a side of the orifice on the patient's side of the mask to an atmosphere side of the orifice, the cross-sectional contour remaining substantially constant in size as gas is passed therethrough.

14. A vent assembly as in claim 13, wherein the insert is formed from a material selected from the group consisting of Silastic™ and Santoprene™.

15. A vent assembly as in claim 13, wherein the insert is substantially crescent-shaped and includes a plurality of orifices therethrough.

16. A vent assembly as in claim 13, wherein the insert includes a groove around a periphery of the insert, the groove being adapted to locate the insert against a correspondingly sized rim of the mask vent opening.

17. A vent assembly as in claim 13, wherein the insert is selected from a shape consisting of substantially circular, triangular, cross or peanut shaped.

18. A vent assembly as in claim 13, wherein a portion of the cross-sectional contour of the orifice near the atmosphere side of the orifice is smaller than a portion of the cross-sectional contour of the orifice near the side of the orifice on the patient's side of the mask.

19. A vent assembly as in claim 13, wherein a central portion of the cross-sectional contour of the orifice has a constant diameter.

20. A vent assembly as in claim 13, wherein the cross-sectional contour of the orifice is symmetrical between the side of the orifice on the patient's side of the mask and the atmosphere side of the orifice.

21. A vent assembly as in claim 13, wherein the cross-sectional contour of the orifice is asymmetrical between the side of the orifice on the patient's side of the mask and the atmosphere side of the orifice.

22. A mask assembly for use with a system for supplying breathable gas pressurized above atmospheric pressure to a human patient=3 s airways, the mask assembly including:

a) a mask which is adapted for fluid communication with a gas supply conduit, said mask including an opening therein and having a first thickness in a direction substantially normal to a planar surface of said mask adjacent said opening; and b) an insert of a substantially constant second thickness in said direction formed of an elastomeric material and at least partially positioned within said opening, said insert having at least one orifice therethrough for gas washout, wherein said second thickness is greater than said first thickness.

23. A mask assembly as in claim 22, wherein the mask is formed from an elastomeric material.

24. A mask assembly as in claim 22, wherein the mask is formed from a material that is relatively rigid compared to the elastomeric material of the insert.

25. A mask assembly as in claim 24, wherein the relatively rigid material is polycarbonate and the insert is formed from a material selected from the group consisting of Silastic™ and Santoprene™.

26. A mask as in claim 22, wherein the insert is attachable to the mask.

27. A mask assembly as in claim 26, wherein the mask includes a plurality of said inserts.

28. A mask assembly as in claim 22, wherein the insert is substantially crescent-shaped and includes a plurality of orifices therethrough.

29. A mask assembly as in claim 22, wherein the insert comprises a groove around a periphery of the insert, the groove being adapted to locate the insert against a correspondingly sized rim of the mask opening.

30. A mask assembly as in claim 22, wherein the insert is selected from a shape consisting of substantially circular, triangular, cross or peanut shaped.

31. A mask assembly as in claim 22, wherein a portion of the orifice near an atmosphere side of the mask is smaller than a portion of the orifice near a side of the mask on the patient's side.

32. A mask assembly as in claim 22, wherein a central portion of the orifice has a constant diameter.

33. A mask assembly as in claim 22, wherein a shape of the orifice is symmetrical between a side on the mask or the patient's side and an atmosphere side of the mask.

34. A mask assembly as in claim 22, wherein a shape of the orifice is asymmetrical between a side of the mask on the patient's side and an atmosphere side of the mask.

35. A mask assembly for use with a system for supplying breathable gas pressurized above atmospheric pressure to a human patient's airways, the mask assembly including:
   a) a mask which is adapted for fluid communication with a gas supply conduit, said mask including an opening therein; and
   b) an insert formed of an elastomeric material at least partially positioned within said opening, said insert having at least one orifice therethrough for gas washout in a first direction,
   wherein said mask adjacent said opening has a first thickness in said first direction and said insert adjacent said orifice has a second thickness in said first direction which is greater than said first thickness.

36. A mask assembly as in claim 35, wherein the mask is formed from an elastomeric material.

37. A mask assembly as in claim 35, wherein the mask is formed from a relatively rigid material.

38. A mask assembly as in claim 37, wherein the rigid material is polycarbonate and the insert is formed from a material selected from the group consisting of Silastic™ and Santoprene™.

39. A mask as in claim 35, wherein the insert is attachable to the mask.

40. A mask as in claim 39, wherein the mask includes a plurality of said inserts.

41. A mask assembly as in claim 35, wherein the insert is substantially crescent-shaped and includes a plurality of orifices therethrough.

42. A mask assembly as in claim 35, wherein the insert comprises a groove around a periphery of the insert, the groove being adapted to locate the insert against a correspondingly sized rim of the mask opening.

43. A mask assembly as in claim 35, wherein the insert is selected from a shape consisting of substantially circular, triangular, cross or peanut shaped.

44. A mask assembly as in claim 36, wherein a portion of the orifice near an atmosphere side of the mask is smaller than a portion of the orifice near a side of the mask on the patient's side.

45. A mask assembly as in claim 35, wherein a central portion of the orifice has a constant diameter.

46. A mask assembly as in claim 35, wherein a shape of the orifice is symmetrical between a face side of the mask and an atmosphere side of the mask.

47. A mask assembly as in claim 35, wherein a shape of the orifice is asymmetrical between a side of the mask on the patient's side and an atmosphere side of the mask.

48. a mask assembly for use with a system for supplying breathable gas pressurized above atmospheric pressure to a human patient's airways, the mask assembly including:
   a) a mask including an interior chamber which is adapted for fluid communication with a gas supply conduit, said mask including an opening therein between the interior chamber and atmosphere and having a thickness in a direction substantially normal to a surface of said mask adjacent said opening; and
   b) an insert of an elastomeric material, the insert at least partially positioned within said opening having at least one orifice therethrough for gas washout,
   wherein the orifice has a length which is greater than said thickness.

49. A mask assembly as in claim 48, wherein the mask is formed from an elastomeric material.

50. A mask assembly as in claim 48, wherein the mask is formed from a material that is relatively rigid compared to the elastomeric material of the insert.

51. A mask assembly as in claim 50, wherein the relatively rigid material is polycarbonate and the insert is formed from a material selected from the group consisting of Silastic™ and Santoprene™.

52. A mask assembly as in claim 48, wherein the insert is attachable to the mask.

53. a mask assembly as in claim 52, wherein the mask includes a plurality of said inserts.

54. A mask assembly as in claim 48, wherein the insert is substantially crescent-shaped and includes a plurality of orifices therethrough.

55. A mask assembly as in claim 48, wherein the insert comprises a groove around a periphery of the insert, the groove being adapted to locate the insert against a correspondingly sized rim of the mask shell opening.

56. A mask assembly as in claim 48, wherein the insert is selected from a shape consisting of substantially circular, triangular, cross or peanut shaped.

57. A mask assembly as in claim 48, wherein a portion of the orifice near an atmosphere side of the mask is smaller than a portion of the orifice near a side of the mask on the patient's side.

58. A mask assembly as in claim 48, wherein a central portion of the orifice has a constant diameter.

59. A mask assembly as in claim 48, wherein a shape of the orifice is symmetrical between a side of the mask on the patient's side and an atmosphere side of the mask.

60. A mask assembly as in claim 48, wherein a shape of the orifice is asymmetrical between a side of the mask on the patient's side and an atmosphere side of the mask.

61. A mask assembly for use with a system for supplying breathable gas pressurized above atmospheric pressure to a human or animal patient's airways, the mask assembly comprising:
   (a) a gas supply conduit,
   (b) a mask which is in fluid connection with the gas supply conduit,
   (c) a region of the gas supply conduit defining a first venting orifice adapted for gas washout, and
   (d) an insert formed of an elastomeric material positioned within said first venting orifice, said insert having at least one orifice therethrough for gas washout, said at least one orifice having a cross-sectional contour from a side of the orifice on the patient's side of the mask to an atmosphere side of the orifice, the cross-sectional contour remaining substantially constant in size as gas is passed therethrough.

62. A mask assembly as in claim 61, wherein the mask is formed from an elastomeric material.

63. A mask assembly as in claim 61, wherein the mask is formed from a material that is relatively rigid compared to the elastomeric material of the insert.

64. A mask assembly as in claim 63, wherein the relatively rigid material is polycarbonate and the insert is formed from a material selected from the group consisting of Silastic™ and Santoprene™.

65. A mask assembly as in claim 61, wherein the insert is substantially crescent-shaped and includes a plurality of orifices therethrough.

66. A mask assembly as in claim 61, wherein the insert comprises a groove around a periphery of the insert, the groove being adapted to locate the insert against a correspondingly sized rim of the first venting orifice.

67. A mask assembly as in claim 61, wherein the insert is selected from a shape consisting of substantially circular, triangular, cross or peanut shaped.

68. A mask assembly as in claim 61, wherein the conduit includes a plurality of said inserts.

69. A mask assembly as in claim 61, wherein the mask also includes at least one venting orifice and a further and said insert positioned therein.

70. A mask assembly in claim 61, wherein a portion of the cross-sectional contour of the orifice near the atmosphere side of the orifice is smaller than a portion of the cross-sectional contour of the orifice near the side of the orifice on the patient's side of the mask.

71. A mask assembly as in claim 61, wherein a central portion of the orifice contour has a constant diameter.

72. A mask assembly as in claim 61, wherein the orifice contour is symmetrical between the face side of the orifice and the atmosphere side of the orifice.

73. A mask assembly as in claim 61, wherein the orifice contour is asymmetrical between the face side of the orifice and the atmosphere side of the orifice.

74. A mask assembly for use with a system for supplying breathable gas pressurized above atmospheric pressure to a human's airways, the mask assembly comprising:

(a) a mask formed of a relatively rigid material, the mask being adapted for fluid connection with a gas supply conduit, (b) a region of the mask defining a first venting orifice adapted for gas washout, and (c) an insert formed of an elastomeric material positioned within said first venting orifice, said insert having two orifices therethrough for gas washout, each said orifice having an asymmetrical cross-sectional contour from a side of the orifice on the patient's side of the mask to an atmosphere side of the orifice, the cross-sectional contour remaining substantially constant in size as gas is passed therethrough, the insert also including a groove around a periphery of the insert, the groove being adapted to locate the insert against a correspondingly sized rim of the first venting orifice.

75. A mask assembly for use with a system for supplying breathable gas pressurized above atmospheric pressure to a patient's airways, the mask assembly comprising:

a) a mask having an inlet tube adapted for fluid connection with a gas supply conduit;

b) a first venting orifice for gas washout formed in the mask; and c) an insert formed of an elastomeric material positioned within the first venting orifice, said insert having at least one orifice formed therethrough for gas washout, said at least one orifice having a cross-sectional contour from a first side of the orifice of the patient's side of the mask to a second side of the orifice on the atmospheric side, the cross-sectional contour remaining substantially constant in size as gas is passed therethrough, wherein:

the mask is formed from a material that is relatively rigid compared to the elastomeric material of the insert, the insert includes a groove around a periphery of the insert, the groove being adapted to locate the insert against a correspondingly sized rim of the first venting orifice, a size of first side of the orifice is different from a size of the second side of the orifice, the first side of the orifice being larger than the second side of the orifice, a portion of the orifice between the first and second sides varying in size along a length thereof, and the mask has a first thickness adjacent the mask orifice that is less than a second thickness of the insert.

76. A mask assembly as claimed in claim 75, wherein the mask includes one of a face mask, a nose mask, a mouth mask and nasal pillows.

\* \* \* \* \*

UNITED STATES PATENT AND TRADEMARK OFFICE
CERTIFICATE OF CORRECTION

| | | |
|---|---|---|
| PATENT NO. | : 6,561,190 B1 | Page 1 of 1 |
| APPLICATION NO. | : 09/021541 | |
| DATED | : May 13, 2003 | |
| INVENTOR(S) | : Kwok et al. | |

It is certified that error appears in the above-identified patent and that said Letters Patent is hereby corrected as shown below:

Column 3, line 53, after "rim 28." insert:

> As seen in Figure 8, orifice 22 has a cross-sectional contour from a face side of the orifice to an atmosphere side of the orifice. In Figure 8, the contour is shown as being symmetrical between the face side of the orifice and the atmosphere side of the orifice with a central portion of the orifice contour being of constant diameter. After the insert 20 is positioned in opening 26 of mask shell 12, the contour remains substantially constant in size as gas is passed therethrough.

Signed and Sealed this

Twenty-fourth Day of October, 2006

JON W. DUDAS
*Director of the United States Patent and Trademark Office*